United States Patent

Barra et al.

[11] Patent Number: 5,843,088
[45] Date of Patent: Dec. 1, 1998

[54] TOOL AND METHOD FOR INSTALLATION OF A VENTRICULAR CANNULATION DEVICE

[75] Inventors: Jean-Aubert Barra, Brest Cedex; Rene Paillot, Orly, both of France

[73] Assignees: Ela Medical SA, Montrouge; Institute de La Sante et de la Recherche Medical, Paris, both of France

[21] Appl. No.: 468,553

[22] Filed: Jun. 6, 1995

Related U.S. Application Data

[62] Division of Ser. No. 995,047, Dec. 22, 1992.

[30] Foreign Application Priority Data

Dec. 23, 1991 [FR] France ............................. FR 91/15981

[51] Int. Cl.⁶ ............................. A61N 1/362; A61M 1/10; A61M 31/00
[52] U.S. Cl. ............................. 606/108; 600/16; 606/1; 623/3; 604/49
[58] Field of Search ................ 606/1, 108; 600/16, 600/17; 601/153; 623/3; 604/49, 8

[56] References Cited

U.S. PATENT DOCUMENTS

| | | |
|---|---|---|
| 2,638,901 | 5/1953 | Sugarbaker . |
| 3,316,914 | 5/1967 | Collito . |
| 3,540,451 | 11/1970 | Zeman . |
| 3,739,750 | 6/1973 | Shinjo . |
| 4,368,736 | 1/1983 | Kaster ................................ 128/334 C |
| 4,836,204 | 6/1989 | Landymore et al. . |
| 5,234,447 | 8/1993 | Kaster et al. . |
| 5,456,714 | 10/1995 | Owen ......................................... 604/8 |

FOREIGN PATENT DOCUMENTS 8201644  5/1982  WIPO .

*Primary Examiner*—Robert A. Hafer
*Assistant Examiner*—Benjamin Koo
*Attorney, Agent, or Firm*—Orrick, Herrington & Sutcliffe, LLP

[57] ABSTRACT

A ventricular cannulation device. An inner part is placed in the cardiac chamber and an outer part is placed outside the cardiac wall. Each of the inner and outer parts is equipped with means for catching onto the cardiac wall. The inner part bears a means for guiding and attaching the outer part thereto. A tube corresponding to the opening of the cardiac wall serves as a support for an outer tube or a vascular prosthesis. A blood circulatory assistance system is provided using a bio-pump, made from the patient's muscle, and a pulse generator to stimulate the bio-pump under program control, to pump blood from the ventricle. Vascular prosthesis are used to connect the cannulation device and the bio-pump with the aorta for blood flow therethrough.

23 Claims, 5 Drawing Sheets

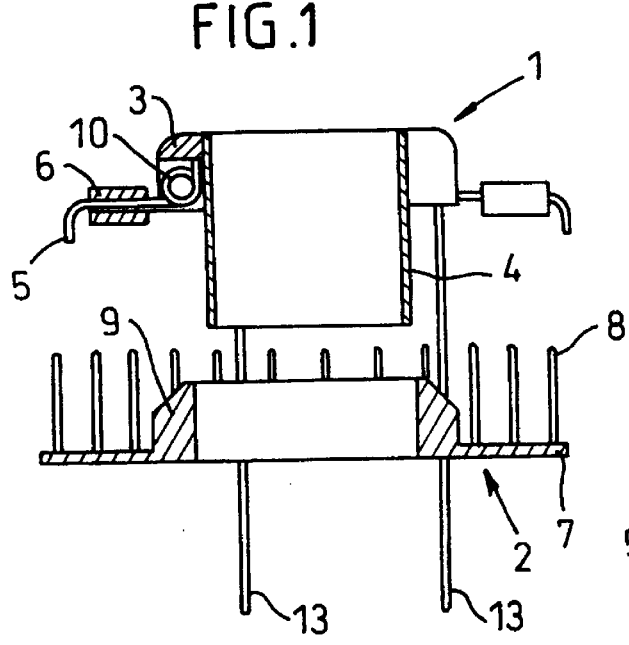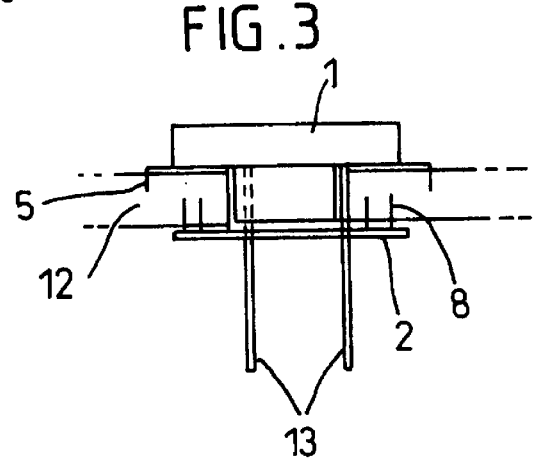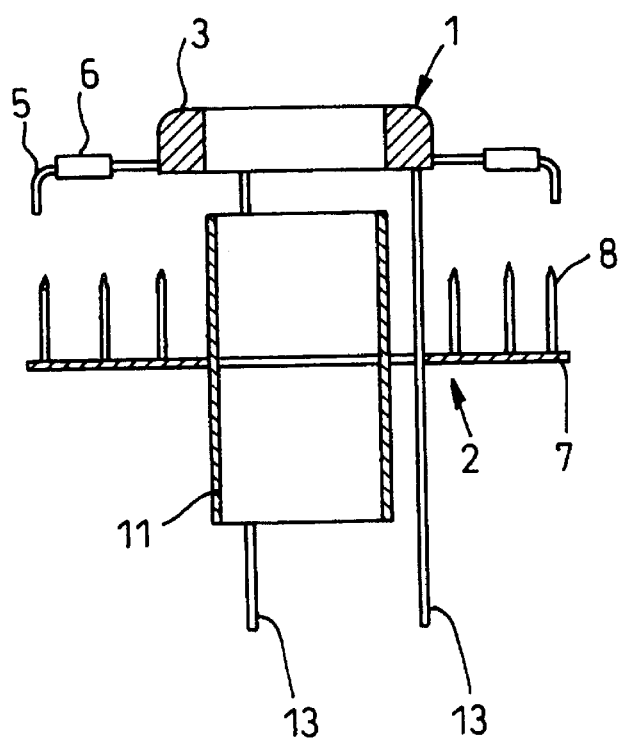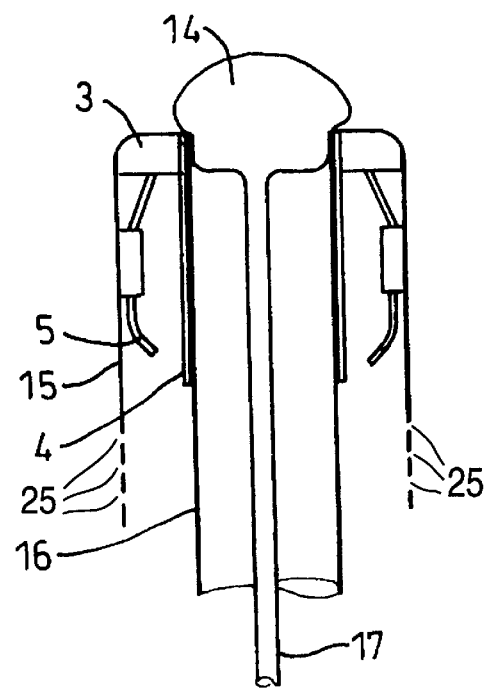

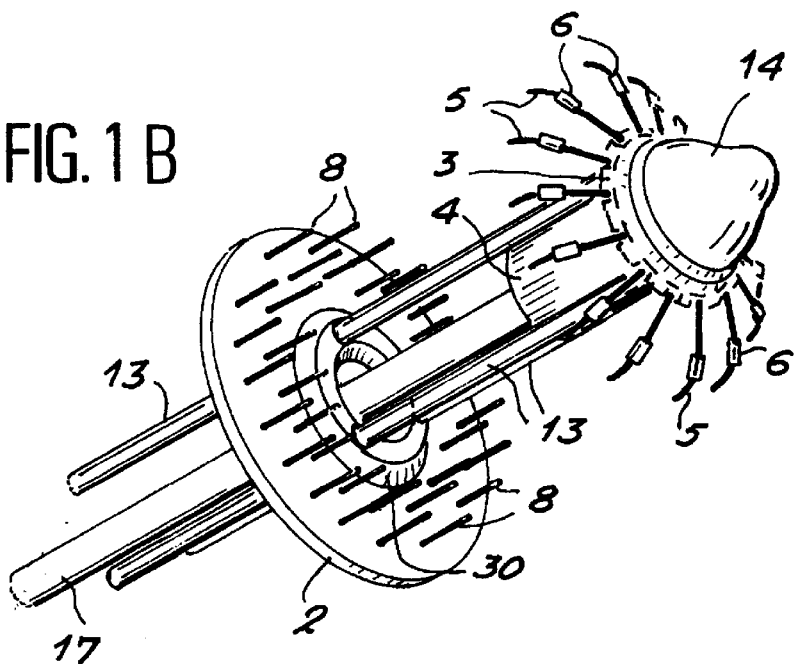
FIG. 1B
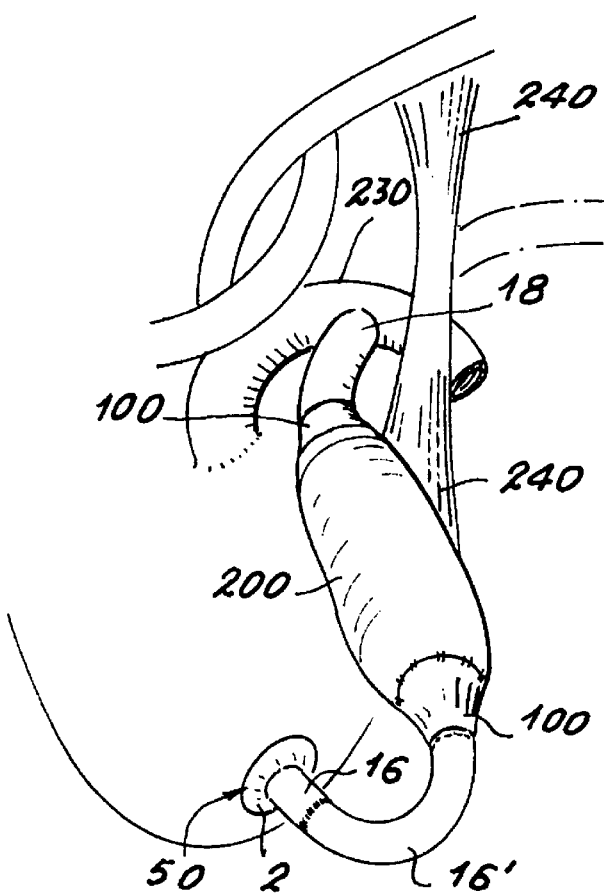
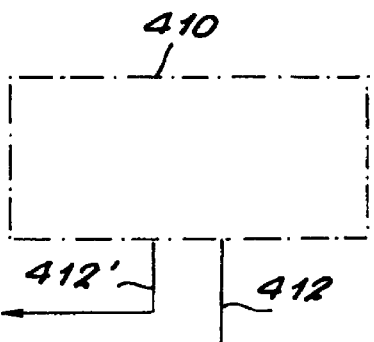
FIG. 7

TOOL AND METHOD FOR INSTALLATION OF A VENTRICULAR CANNULATION DEVICE

This is a divisional of copending application(s) Ser. No. 07/995,047 filed on Dec. 22, 1992.

BACKGROUND OF THE INVENTION

This invention relates to a cardiac cannulation device, its use, and a circulatory assistance system using the cannulation device, a bio-pump, and a stimulation pulse generator, more particularly to a ventricular cannulation device.

In certain cases of heart-failure, it is a known procedure to draw blood from the left ventricle for reinjection into the aorta, possibly after passing through a pump. The blood is drawn through a tube connected to a port formed in the left ventricle, passed through a pump, and reinjected by a tube into the aorta at a point situated downstream of the point of insertion of the tube.

According to a recently developed method, the blood is drawn directly from the left ventricle through the cardiac wall, and circulates in a vascular prosthesis before being reinjected into the aorta.

Establishing communication through the cardiac wall poses a certain number of problems relating to the fact that the wall, which has a thickness in the region of 1.5 cm, is constantly in motion. In particular, it is indispensable that the communication be established under strict tightness conditions.

SUMMARY OF THE INVENTION

It is an object of the present invention to provide a device ensuring communication through the cardiac wall between the cardiac chamber and a vascular prosthesis, with sufficient safety to fulfill the tightness condition. It is another object to provide such a device that can be quickly and easily inserted and secured. It is another object to provide a device and method of installation which does not require extracorporeal blood flow during the procedure.

It is another object of the invention to provide a system for assisting the blood circulation from the cardiac chamber, through the vascular prosthesis into the aorta, under period pumping conditions utilizing stimulating pulses to control the pumping.

Broadly, one aspect of the present invention concerns a cannulation device for ensuring communication through the cardiac wall, between a cardiac chamber and a vascular prosthesis. One such cannulation device includes:

an inner part, to be placed inside the cardiac chamber;

an outer part, to be placed outside the cardiac wall, the inner and outer parts each being equipped with means for catching onto the cardiac wall, said inner part having means for guiding and securing said outer part; and a tube corresponding to the opening of the cardiac wall and serving as a support for a vascular prosthesis.

In a preferred embodiment, the inner part is crown-shaped and its catching means is in the shape of a plurality claws that extend around the crown. Each claw bears a pad of relatively greater surface area for resting against the cardiac wall tissue. More preferably, the claws have a netting in biocompatible material to provide a more effective seal. In a preferred embodiment, the claws can be folded into the space requirements of the crown for the purpose of inserting the inner part into the cardiac chamber. Following insertion, the claws are allowed to extend. The claws may extend radially from the crown perimeter. They also may extend in a spiral or helical direction, e.g., like the spokes of a wheel.

The outer part is preferably disk-shaped and its catching means is comprised of a plurality of needles perpendicular to the disk. The disk preferably bears the tube and, the tube is preferably interdependent with, i.e., bonded to, the inner crown.

The means for guiding and attaching the outer part is comprised of rods, e.g., 2 or 3 rods, that can be blocked, preferably by crimping, and cut after positioning of the device on the cardiac wall. The rods are secured at one end to the inner part and pass through suitable apertures in the outer part.

The central opening of the inner part crown is plugged throughout the positioning of the device. This facilitates insertion and minimizes uncontrolled leakage of blood out of the cardiac chamber. A removable solid or inflatable stopper may be used to plug the crown opening.

Another aspect of the invention is directed to a system for assisting blood circulation comprising a ventricular cannulation device, a first vascular prosthesis having a one-way flow valve, a second vascular prosthesis having a one-way flow valve, and a programmable stimulation pulse generator, wherein the second vascular prosthesis extends into the descending thoracic aorta, the first vascular prosthesis is secured to the ventricular cannulation device, the first and second prosthesis are connected to a bio-pump formed from the patient's muscular tissue to pass blood only from the ventricle to the aorta. The stimulation pulse generator stimulates the bio-pump to contract, in the same manner that a pacemaker would stimulate a ventricle, thereby to pump blood from the ventricle to the aorta.

Yet another aspect of the invention concerns a tool for use in installing the ventricular cannulation device, and methods of installation.

BRIEF DESCRIPTION OF THE DRAWINGS

Further features and advantages of the invention will be apparent from the following detailed description of several preferred embodiments of this invention taken in conjunction with the accompanying drawings, in which like reference characters refer to like parts throughout, and in which:

FIG. 1a is a top view of an alternate embodiment of the inner part of FIG. 1;

FIG. 1b is an elevated perspective view of the device of FIG. 1;

FIG. 2 is a schematic view of an axial section of a second embodiment of the ventricular cannulation device embodying the invention;

FIG. 3 is a schematic diagram of an axial section of the relative disposition of the cardiac wall and the secured cannulation device embodying the invention;

FIG. 4 is a schematic diagram of an embodiment of the inner part of the cannulation device prior to insertion into the ventricle;

FIG. 7 is a schematic drawing of a stimulation pulse generator controlled circulatory assist system of the present invention.

DETAILED DESCRIPTION OF THE INVENTION

Figure 1:
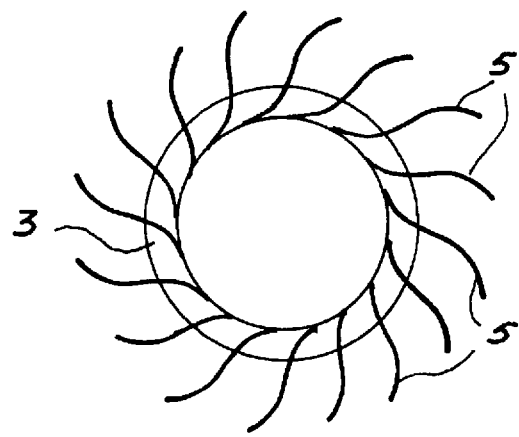
FIG. 1 is a schematic view of an axial section of a first embodiment of the ventricular cannulation device embodying the invention.

Referring to FIGS. 1 and 1b, a ventricular cannulation device in accordance with a preferred embodiment in the present invention is shown. The device comprises an inner part 1, to be placed in the ventricular chamber, and an outer part 2, to remain outside the ventricular wall. Referring to FIG. 7, a ventricular device 50 in accordance with the present invention is installed in the ventricle LV, of which the outer part 2 is outside the heart, is illustrated. Referring to FIG. 3, it is shown how the inner part 1 and the outer part 2 are on opposite sides of the ventricular wall 12.

The inner part 1 is comprised of a crown 3 and a portion of tubing 4 disposed inside crown 3 and protruding outwardly from the ventricular chamber. Tube 4 supports or carries a vascular prosthesis 16 (See FIGS. 4 and 7) which is secured, e.g., by bonding, either to the inside or to the outside of tube 4. In crown 3 are disposed a plurality of claws 5, oriented towards cardiac wall 12 and constituting a means for catching inner part 1 to cardiac wall 12. As illustrated in FIG. 3, the end portion of claws 5 are designed to penetrate into cardiac wall 12. This is to minimize any lateral motion of crown 3 relative to the cardiac wall 12.

Claws 5 are comprised of a springy metal wire, preferably forming a spiral spring element 10 inside the thickness of crown 3. This biases the tip of claw 5 in penetrating contact with cardiac tissue 12. Each claw 5 also has in its substantially rectilinear upper part a pad 6 which is intended to rest on cardiac wall 12 and has a relatively large surface area. Pad 6 may be a piece of biocompatible material placed about the wire of claw 5 or a thickened or flattened portion of metal wire.

Outer part 2 is in the shape of a disk 7 carrying a plurality of needles 8. Needles 8 are oriented towards cardiac wall 12 to penetrate into wall 12 and constitute the means for catching the outer part 2 to cardiac wall 12. The disk 7 has a central opening that is sufficient to let tube 4 (and prosthesis 16) pass. Around this central opening is provided a substantially cylindrical sleeve 9, intended to partially cover tube 4. Sleeve 9 enables tube 4 and vascular prosthesis 16 to slide in compliantly in frictional contact.

The two parts 1 and 2 are respectively put into position, one inside the ventricular chamber and the other on the outside, and are fastened together while maintaining cardiac wall 12 between them by means of the claws 5 and needles 8. Cardiac wall 12 is thus tightly confined around the tube 4 which ensures the passage of the ventricular blood through tube 4.

The metal wire constituting claws 5 is secured to the upper part (on FIG. 1) of the crown 3. It is coiled to constitute spiral spring 10 and to spread radially with regard to the axis of crown 3. At rest, claws 5 together form a sort of opened umbrella structure, and each claw 5 tends to return to its rest position when it has been mechanically stressed out of this position.

Claws 5 may be strictly radially directed from inner part 1, and alternately may extend at an angle to a radius, e.g., in a helical or spiral manner as illustrated in FIG. 1a. Further, claws 5 may fold or compress at an angle to the axis of inner part 1, rather than in a plane that is normal to the circumference of inner part 1. In other words, the claws 5 move along a path that is not parallel to the longitudinal axis of the connector, along which the obturator tube 17 lies as illustrated in FIG. 1b, but rather follows a path that is in a plane at an angle to that axis.

Figure 1C:
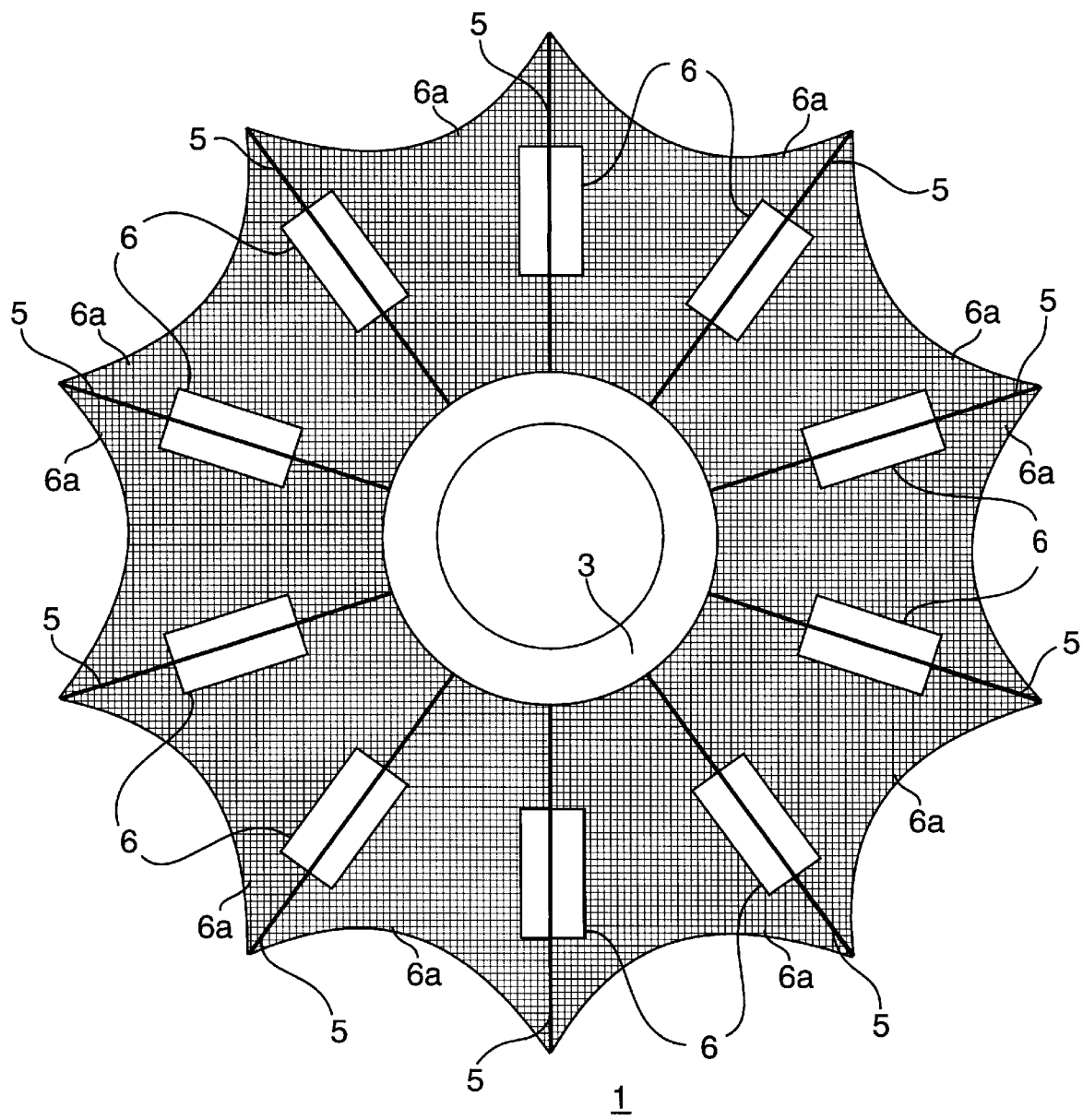
FIG. 1c is a top view of a second alternate embodiment of the inner part of FIG. 1.

Advantageously, as illustrated in FIG. 1c, all claws 5 have a netting of biocompatible material 6a, which unfurls like the fabric of an umbrella to provide a more intimate connection with cardiac wall 12 (not shown). Furthermore, to avoid a thrombogenic effect, inner part 1 can be covered with a conventional biocompatible covering.

An alternate embodiment of the present invention is shown in FIG. 2. In this embodiment inner part 1 has the same crown 3 and claws 5 as the embodiment illustrated in FIG. 1, but no longer carries tube 4. Outer part 2 comprises the same disk 7 and needles 8 as the embodiment illustrated in FIG. 1, but no longer has sleeve 9. Instead, a tube 11 is provided interdependent with the disk 7 and serves as a support for the outer tube.

The present invention also is shown in FIG. 3. In this embodiment, the two parts 1 and 2 of the device are seen placed on either side of cardiac wall 12 which has been incised beforehand. Cardiac wall 12 then has a circular opening of diameter corresponding substantially to that of tube 4 (or 11). Inner part 1 is placed in the ventricular chamber, with outer part 2 being placed outside the chamber. Needles 8 and claws 5 penetrate cardiac wall 12 in order to grip it efficiently.

In order to tighten inner part 1 and outer part 2 of the device into one another, a number of rods 13 are provided, preferably, 3 in number. Rods 13 are interdependent with inner part 1. Rods 13 pass through outer part 2, through holes provided for this purpose, and have a diameter just barely sufficient to enable rods 13 to pass therethrough. Thus, when inner part 1 is practically in position, outer part 2 is in turn put into position by sliding along the rods 13. When the two parts 1 and 2 clasp cardiac wall 12 and maintain it satisfactorily, rods 13 are blocked at the level of disk 7, e.g., by crimping or crushing. The excess lengths are then cut off.

Referring to FIGS. 1b and 4, in order to have inner part 1 penetrate the cardiac chamber, a solid or inflatable stopper 14, also known as an obturator, is first placed in its axial opening, thereby sealing the central opening (FIG. 4). Furthermore, claws 5 are folded back towards tube 4 (or 11), and a sleeve 15 is put in place, having dimensions which corresponds to the perimeter of the crown 3, e.g., a cylindrical sleeve. The purpose of cylinder 15 is to keep claws 5 folded back, within the space requirements of the crown 3, so as to pass them through cardiac wall 12. When the upper edge of cylinder 15 is in the cardiac chamber, crown 3 is made to advance inside the chamber, e.g., by action on the rods 13, so as to free claws 5 which take up their opened umbrella position. See FIGS. 1a and 1b. Cylinder 15 is subsequently removed. Outer part 2 is then put into position and secured, e.g., by crimping, and rods 13 are cut.

Advantageously, outer part 2 is put into a standby position on rods 13 before the intervention, and a tool 300 is provided to ensure the progression of the outer part 2 along the rods 13 towards the cardiac wall.

In FIG. 4, stopper 14 represented as of the inflatable type. An inflation tube 17 is disposed inside vascular prosthesis 16, and remote inflation and deflation means are provided.

To draw the blood from the cardiac chamber, stopper 14 is removed, e.g., after deflation, when applicable.

Each of parts 1 and 2 of the ventricular cannulation device can advantageously have, on its side resting against cardiac wall 12, a hoop or ring 30 of biocompatible material having a certain flexibility (shown in FIG. 1b). Hoop or ring 30 acts as tightness joint ring, and also acts as a damper when the device is put into position, in order to minimize crushing of cardiac wall 12.

One application of the ventricular cannulation device is for use in a biochemical circulatory assistance system (BCAS) that uses the strength of the musculus latissimus dorsi (MLD) as a bio-pump to force blood flow. The MLD is serially connected between the tip of the left ventricle LV and the descending thoracic aorta (DTA) 230.

The BCAS comprises a contractile muscular chamber (CMC) referred to as a bio-pump 200, which is linked via a connector 100 to a first valved vascular prosthesis 16', optionally connected to prosthesis 16, which is implanted at the tip of the left ventricle by means of the ventricular cannulation device ("VCS") 50 of the present invention, and linked via a connector 100 to a second valved vascular prosthesis 18 anastomosed at the lateral end with the descending thoracic aorta 230.

Bio-pump 200 is achieved by a winding of the MDL which maintains its vasculo-nerval pediculus. It is roughly cylindrical in shape and delimits a cavity which is 12 cm long and has a cross section of 4 cm (150 ml volume). The internal wall of the bio-pump 200 will be directly in contact with the circulating blood. The autologous muscle is less thromgonic than a prosthetic tube compressed by muscle. Moreover, this internal wall could be covered with endocardial cells developed from previously grafted island of endocardial cells.

The vascular prosthesis tubes 16, 16' and 18 are made from polyethylene terephthalate as under the trade name DACRON or of a similar type, or expanded polytetrafluoroethylene, e.g., as under the trade name GORTEX, which protheses materials are known. Tubes 16' and 18 are fitted with a conventional valve imposing a one-way direction on the blood flow, namely from the left ventricle to the descending thoracic aorta.

Bio-pump 200 will be respectively fitted at its ends with two cone-shaped prosthetic connections 100, attached, e.g., sutured, to the circular banks of the MLD tissue. The fibrous colonization of these cone connectors 100 from the muscle will ensure tightness and the solidity of fixation at the muscle-prosthesis interface.

Figure 5:
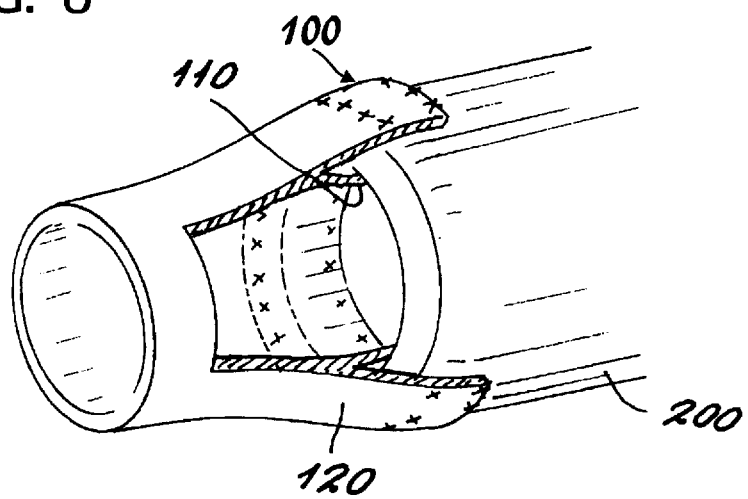
FIG. 5 is an elevated perspective cutaway view of a connector for connecting a vascular prosthesis to a bio-pump.

Referring to FIG. 5, each connector 100 is composed of a cylindrical internal part 110, which is attached to the inner wall of the bio-pump 200, and covered by a conical part 120, which is fixed to the outer wall of the bio-pump 200. These prosthetic parts are manufacturable in velvet made of a material such as DACRON polyester fibers (hereinafter referred to as "Dacron velvet" to ensure excellent anchoring, over approximately 1 cm at the ends of the muscle tissue. The valved prosthetic tubes 16' and 18 will thus be sutured end-to-end to connectors 100.

The connection between the left ventricle LV and the first vascular prosthesis 16 will be ensured by VCS 50. VCS 50 is installed using inner and outer parts 1 and 2, an introductory sheath 15, an obturation ball stopper 14, and an insertion tool 300.

Figure 6:
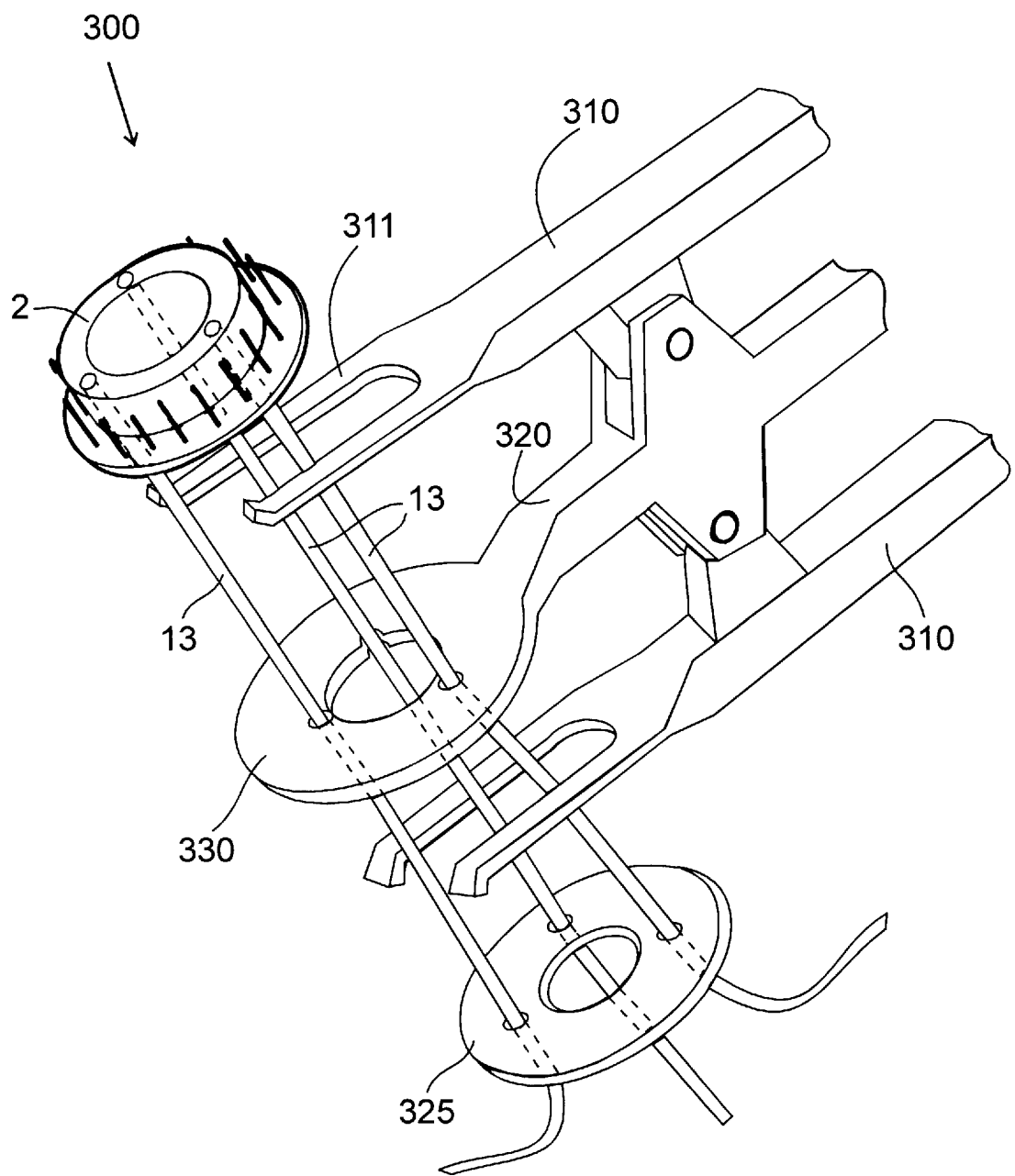
FIG. 6 is a partial perspective view of a tool for installing a ventricular cannulation device.

Referring to FIG. 6, tool 300 enables the inner and outer parts 1 and 2 to be latched together, sandwiching the myocardium 12 of the left ventricle LV between them. It enables outer part 2 to be slid smoothly along the three rods 13 supported by inner part 1. Tool 300 is comprised of two levers 310, each supporting at one end a contacting surface 311, and a central arm 320 supporting a rod guide ring 330. The inner part 1 (not shown in FIG. 6), the outer part 2 and tool 300 are slid onto three rods 13 extending from inner part 1, and assembled together prior to insertion. A ring 325, which is slipped on and attached distally to the three rods 13, e.g., by crimping, makes the assembly parts interdependent and serves as a counter bearing when tool 300 is closed by squeezing the distal ends of levers 310 together. Simple single-handed pressure on the two lever handles 310 will enable the inner and outer parts 1 and 2 to fit into one another, as well as a tightening adjustment pressure. Each of levers 310 supports a contacting surface in the shape of a two-pronged fork 311 of different size. One fork 311 is of smaller dimensions (width) than the other lever handle fork 311, which enables the two forks 311 to overlap one another when tool 300 is open (not compressed). The one lever fork 311 thus comes to rest against the outer part 2 and the other lever similarly comes to rest with its fork on the counter bearing ring 325.

The central arm 320 supports a slide guide ring 330 which slips onto the three rods 13. At the tail of arm 320 is a catch which enables it to become interdependent with the other lever handle 311. A cylindrical insertion sheath 15, which is constructed to be retracted by symmetrical tearing along a perforated longitudinal axis namely sheath 15 is provided with perforations 25 (shown in FIG. 4), enables the retractile claws 5 of inner part 1 to be contained and optionally to maintain the outer part 2 axially folded during insertion. Obturation ball 14 blocks the opening of crown 3 of inner part 1.

Referring to FIG. 7, a controllable stimulation pulse generator 410 and electrodes 412 are used for enabling the bio-pump 200 to be conditioned and stimulated during ventricular diastole to pump blood. The descending thoracic aorta is illustrated as reference 230.

The surgical technique for implanting the BCAS in human beings involves two surgical stages situated approximately 7 weeks apart.

The first surgical stage is production of the contractile muscular pouch to form bio-pump 200. The approach is via the latarothoracic path. The musculus latissimus dorsi is disinserted from its distal rachidian ties. The bio-pump 200 is made by a winding the muscle about itself in a manner that maintains its vasculo-nerval pediculus 240 intact. The cone-shaped connectors 100 are stitched to the ends of the muscular tube of bio-pump 200. The entire bio-pump muscular chamber, including the inner side 110 (not shown in FIG. 7, shown in FIG. 5) of the conical prostheses, is rested against an internal template (not shown). The latter molds the inner chamber of the muscular pouch/conical prostheses assembly. This template is inflatable and will be removed at a later stage by simple deflation.

A first stimulation electrode 412 is placed near or on the nerve 240 of bio-pump 200, with a second electrode 412' placed a few centimeters away. Electrodes 412 and 412' are connected to the pulse generator 410 which is implanted beneath the skin of the abdomen.

This first procedure is followed by a cicatrization period, during which nothing is undertaken for about ten days. During this period, the sutures cicatrize, muscle/muscle in the case of the pouch, and Dacron/muscle in the case of connectors 100. Furthermore, during this period the fibrous tissue invades the Dacron velvet, which entails excellent fixing of the conical prosthetic to the muscle tissue and produces final proofing of the cone-shaped connectors. The muscular pouch is lodged in a silastic bag (not shown) with a very thin wall. This bag avoids adhesion between subcutaneous tissue and the muscle. This enables the pouch to be moved at a later stage without causing surgical injury. The skin is closed over the assembly thus carried out.

After the cicatrization period, a bio-pump conditioning period occurs during which the skeletal muscle is conditioned until it gradually becomes fatigue-resistant. The pulse generator 410 is programmed for this purpose to define a suitable mode of muscular stimulation, in accordance with the level of skill in the art. The conditioning period lasts five weeks.

The second surgical stage concerns a large left anterolateral thoracotomy. This extensively reveals the tip of the left ventricle LV and the descending aorta 230.

The muscular pouch is mobilized. The ease of this manoeuver is enhanced by the fact that the muscle is surrounded by the siliastic bag, thus avoiding adhesion between the pouch and the surrounding tissue. The muscular pouch is then transplanted inside the thorax. To do so, the second or third rib likely will be partially removed. The pediculus 240 of the MLD maintains its upper vascular and nerval ties.

The left ventricle connector VCS 50 is then implanted. All the elements previously described are in the form of a two-ended candle. The plugged ventricular end, is comprised of an inflatable ball 14 used to obstruct the connector. The two-pronged tool 300 is attached to the opposite end. The body of the candle is delimited by the above-mentioned sheath 15. A small incision is made with a surgical knife at the tip of the left ventricle LV. Hemostasis may be achieved by digital pressure or other well-known technique. The small incision is enlarged by a metal or titanium plastic candles of increasing diameter (not shown). Bleeding between candle changes is not very abundant. The diameter of the biggest candle is approximately 2 cm. This opening then serves to introduce into the left ventricle the inner part 1 of ventricular connector VCS 50 supporting prosthetic tube 16 of diameter equal to that of the valved tubes 16' and 18.

After insertion of the VCS 50 inner part 1 into the left ventricle LV, outer sheath 15 is drawn out of and torn symmetrically along the perforated longitudinal axis. This produces two consequences. On the one hand, it enables claws 5 inside the left ventricle to unfold, and, on the other hand, it frees outer part 2. This manoeuver is very quick. It is then sufficient to press the two pronged tool 300 to push the outer part 2 towards the inner part 1. The latter is separated from the former by the myocardial muscle 12 which tautens over the tube 4 (or 11) or prosthetic tube 16.

When the myocardial muscle 12 is well sandwiched between the inner and out parts 1 and 2 of VCS 50, a system for crimping and cutting the axes or a catching system fastens the two parts together in this position (not shown). The tool 300 used to implant the connector (i.e., axes, handles 310, outer sheath 15) detaches itself. All that remains to be done is to purge the prosthesis 16 that is interdependent with VCS 50 and the obturator plug 14.

Only a few minutes are required to implant VCS 50, i.e., less than five or six minutes. The implantation is performed on a patient having undergone moderate anticoagulation (heparin), without recourse to extracorporeal circulation.

Prosthetic tube 16 of the ventricular connector is stitched, by hand or automatically, to valved tube 16' which is in turn attached in an identical manner to the end of the conical prosthesis 100 adjoining the contractile pouch which is then in its intrathoracic position. The contractile pouch will be freed from its internal template, which is deflated for this purpose and removed.

The second valved tube 18 will then be stitched identically to the other end (so-called distal end) of the muscular pouch by means of the aforementioned conical connection 100.

Stitching of the distal valved tube 18 to the descending thoracic aorta 230 will be performed conventionally by manual termino-lateral stitching to the laterally clamped descending thoracic aorta 230.

At the end of the second surgical stage, after purging the air from the blood circuit, the bio-pump 200 and therefore the contractile muscular pouch can be stimulated immediately. Circulatory assistance therefore commences immediately, even before the thorax is closed. It should be noted that the chronology of the various surgical stages of this second surgical operation can be modified according to the patient's general condition or to local conditions of the thorax. If the patient is very fragile, the implanting of the BCAS can be completed via the left ventricular path. This enables the period of time between cardiac manipulations and the start of circulatory assistance to be reduced to a few minutes (10 to 16).

The stimulation pulse generator 410 recording the ECG and arterial pressure (in real time) should, by means of its program, make the bio-pump 200 muscular pouch contract during the ventricular diastole. A telemetry system using magnetic induction or radio frequency will enable dialogue with the pulse generator 410 by simple positioning of said system on the skin facing the pulse generator 410 without tegumental rupture. The advantages of the BCAS are as follows:

a) the first surgical operation is extrathoracic, minor, without pleural opening;

b) during the second operation, the BCAS is implanted without recourse to extracorporeal circulation;

c) circulatory assistance begins immediately after the ventricular stage of the second operation, even before the thorax is closed, thereby enabling its working to be visually monitored and the first adjustments to be carried out;

d) the one-way flow of the BCAS avoids blood stasis and to-and-fro motion which considerably reduces thrombogenicity;

e) the interior of the bio-pump 200 contractile pouch, i.e., the muscular surface, is directly in contact with the blood. There is no prosthesis or pericardium between the muscle and the blood. The autologous muscle surface is less thrombogenic than either the pericardium or the prosthesis;

f) in the event of a certain degree of thrombogenically, islands of endocardial cells can be grafted to the endovascular side of the contractile pouch, in the region of the conical connections. This grafting of cells cultivated during the cicatrization period can be easily performed during the second surgical operation;

g) the work performed by the conditioned bio-pump does not require any input of energy from without (excluding pulse generator 410).

One skilled in the art will appreciate that the present invention can be practiced by other than the described embodiments, which are presented for purposes of illustration and not of limitation.

We claim:

1. A method for installing a cannulation device in an aperture formed in cardiac tissue comprising:

(a) providing an inner part having a central opening and an outer perimeter dimension, for placement in the cardiac chamber;

(b) providing the inner part with a first means for catching onto the cardiac wall having a normal position for catching tissue and a deformed position in which the first catching means is confined within the perimeter dimension of the inner part;

(c) providing an outer part having a central opening, for placement on the cardiac tissue opposite the inner part;

(d) providing the outer part with a second means for catching the cardiac tissue;

(e) placing a sleeve over the inner part so that the first catching means is in its deformed position confined within the sleeve;

(f) inserting the sleeve through the cardiac tissue aperture so that the inner part passes inside the cardiac chamber;

(g) removing the sleeve while maintaining the inner part inside the cardiac chamber so that the first catching means returns to its normal position; and (h) urging the inner and outer parts together so that the first catching means catches the cardiac tissue from the inside and the second catching means catches the cardiac tissue from the outside and securing the inner and outer parts together to provide the cannulation device.

2. The method of claim 1 wherein step (b) further comprising providing the first catching means as a plurality of claws having tissue penetrating tips.

3. The method of claim 2 wherein the plurality of claws extend radially around the perimeter of the inner part and further comprising providing each claw with a pad for resting against the cardiac wall.

4. The method of claim 2 in which step (b) further comprises providing a netting of a biocompatible material secured to the plurality of claws.

5. The method of claim 1 wherein step (c) further comprises providing the outer part with a disk structure and (d) further comprises providing the second catching means as a plurality of needles extending from the disk structure for passing into the cardiac tissue.

6. The method of claim 1 further comprising (i) providing a tube for supporting a vascular prosthesis and securing the tube to the central aperture of one of the inner and outer parts.

7. The method of claim 1 further comprising occluding the central opening of the inner part during insertion of the inner part.

8. The method of claim 7 in which the occluding step further comprises providing a removable plug in the central opening during insertion and removing the plug after the first and second parts have been secured.

9. The method of claim 7 in which the occluding step further comprises providing an inflatable stopper in the central opening during insertion, and, after the first and second parts have been secured, deflating the inflatable stopper and removing the deflated stopper.

10. The method of claim 1 wherein step (h) further comprises:

providing a guide means secured to the inner part;

mounting the outer part on the guide means for movement therealong towards the inner part; and moving the outer part along the guide means towards the inner part.

11. The method of claim 10 wherein providing a guide means further comprises providing a plurality of rods secured to the inner part and wherein mounting the outer part further comprises providing the outer part with a like plurality of apertures for sliding engagement with the guide rods.

12. The method of claim 11 further comprising blocking or crimping the guide rods after the inner and outer parts have been urged together to hold the inner and outer parts in place.

13. The method of claim 12 further comprising removing the length of the guide rods distal to the blocked or crimped area.

14. The method of claim 11 wherein step (h) further comprises securing a bearing ring to the plurality of guide rods and inserting a tool between the outer part and the bearing ring for urging the outer part toward the inner part along the plurality of guide rods.

15. The method of claim 14 wherein inserting a tool further comprises providing a tool having a first lever and first contacting surface for contacting the outer part, a second lever and second contacting surface for contacting the bearing ring, and a guide ring, providing the guide ring with a plurality of apertures, mounting the first and second levers to move about a pivot, and passing the plurality of guide rods through the plurality of guide ring apertures so that the first and second contacting surfaces are between the outer part and the bearing ring, and moving the first and second levers to separate the first and second contacting surfaces for urging the outer part towards the inner part.

16. The method of claim 15 further comprising securing the guide ring to the second lever for movement therewith.

17. The method of claim 1 wherein step (e) further comprises placing a sleeve having a perforated wall over the inner part and wherein step (g) further comprises tearing the sleeve along the perforated wall prior to removing the sleeve.

18. The method of claim 2 wherein the plurality of claws extend spirally or helically from the perimeter of the inner part.

19. An insertion tool for installing a ventricular cannulation device on opposite sides of a cardiac wall comprising:

a first lever having a first contacting surface;

a second lever having a second contacting surface;

a pivot, wherein at least one of the first and second levers is pivotably connected to said pivot, the first and second contacting surfaces being movable in a range of motion between a first distance of separation and a second distance of separation, the second distance being greater than the first distance; and a ring supporting member having a guide ring at one end, the ring supporting member being connected to said pivot and the guide ring being interposed between said first and second contacting surfaces in said range of motion.

20. The tool of claim 15 in which the cannulation device has an inner part and an outer part, a plurality of guide rods connected to the inner part, and a bearing ring secured to the end of the plurality of guide rods, wherein the guide ring further comprises a plurality of apertures for receiving the guide rods so that the first and second contacting surfaces, when separated by said second distance, fit between the bearing ring and the ventricular cannulation device and, when moved from the second distance to the first distance, urge the inner and outer parts together.

21. The tool of claim 20 wherein the first and second contacting surfaces further comprise first and second forks, respectively.

22. The tool of claim 19 wherein each of the first and second levers is pivotably connected to said pivot.

23. The tool of claim 22 wherein the ring supporting member is integral with said pivot.

* * * * *